United States Patent [19]

Yahner

[11] 4,018,768

[45] Apr. 19, 1977

[54] [1]BENZOTHIENO [3,2-d]-v-TRIAZINES AND SYNTHESIS THEREOF

[75] Inventor: Joseph Andrew Yahner, New Palestine, Ind.

[73] Assignee: Eli Lilly and Company, Indianapolis, Ind.

[22] Filed: Dec. 2, 1975

[21] Appl. No.: 636,885

[52] U.S. Cl. .......................... 260/248 AS; 424/249
[51] Int. Cl.$^2$ ..................................... C07D 253/08
[58] Field of Search .............................. 260/248 AS

[56] References Cited

UNITED STATES PATENTS 3,772,276  11/1973  Sauter ............................... 260/248

OTHER PUBLICATIONS

Beck et al. (I), *J. Org. Chem.*, vol. 39, pp. 3440–3441 (1974).
Beck et al. (II), *J. Org. Chem.*, vol. 38, pp. 2450–2452 (1973).
Taylor and McKillop, "The Chemistry of Cyclic Enaminonitriles and O–Aminonitriles", pp. 225–226, Interscience Pub. (1970), New York.
Kwartler et al., *J. Amer. Chem. Soc.*, vol. 65, pp. 1804–1806 (1943).
Fieser and Fieser, "Advanced Organic Chemistry", pp. 727–728, Reinholdt Pub. (1961).
Konig et al., *Chem. Ber.*, vol. 32, pp. 782–793 (1899).
Erickson et al., "The 1,2,3- and 1,2,4 Triazines, etc.", Interscience Pub., Inc., New York, (1956) p. 31.

*Primary Examiner*—John M. Ford
*Attorney, Agent, or Firm*—Joseph A. Jones; Everet F. Smith

[57] ABSTRACT

A series of [1]benzothieno[3,2-d]-v-triazines are prepared by diazotization of 3-aminobenzo[b]thiophene-2-carbonitriles.

14 Claims, No Drawings

[1]BENZOTHIENO [3,2-d]-v-TRIAZINES AND SYNTHESIS THEREOF

BACKGROUND OF THE INVENTION

This invention belongs to the art of synthetic organic chemistry, and provides a series of new antimicrobial heterocyclic compounds which are prepared by a novel process.

The 3-aminobenzo[b]thiophene-2-carbonitriles which are starting compounds for the process of this invention were disclosed by Beck and Yahner, *J. Org. Chem.* 39, 3440–41 (1974).

Beck and Yahner, *J. Org. Chem.* 38, 2450–52 (1973), showed the synthesis of 9-chloro-3-methyl[1-]benzothieno[3,2-d]-v-triazin-4(H)-one by the diazotization of methyl 3-amino-4-chlorobenzo[b]thiophene-2-carboxamide. The same reference also described the synthesis of benzothienooxazinones and benzothienopyrimidinones.

Benzothieno[3,2-d]triazinones, wherein the substitutable carbon atom of the triazine ring is distant from the sulfur atom of the thiophene ring, are in the art. Sauter et al., *Monatsch. Chem.* 104, 1586–92 (1973) and U.S. Pat. No. 3,772,276. Henriksen et al., *Acta. Chem. Scand.* 26, 3342–46 (1972), taught thieno[3,2-e]-1,2,3-triazin-4-ones and thieno[3,4-e]-1,2,3-triazin-4-ones.

SUMMARY OF THE INVENTION

This invention provides to organic chemists new compounds of the formula

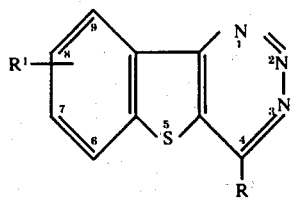

wherein R represents
 hydrogen,
 chloro,
 methoxy,
 ethoxy,
 amino,
 hydrazino,
 methylamino,
 ethylamino,
 dimethylamino or
 diethylamino;
$R^1$ represents
 hydrogen,
 chloro,
 fluoro,
 bromo,
 methyl or
 nitro;
provided that $R^1$ represents hydrogen when R represents a group other than chloro.

The invention also provides a process for the synthesis of a compound of the formula

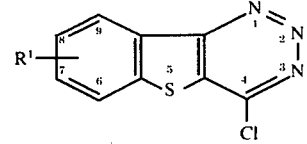

which comprises contacting a compound of the formula

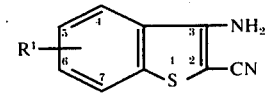

with an alkali metal nitrite and hydrochloric acid at a temperature from about −10° C. to about 25° C.

DESCRIPTION OF THE PREFERRED EMBODIMENT

The following compounds are named to assure that organic chemists understand the invention. The compounds named here should not be understood to bound the scope of the invention, but are merely exemplary of it.

4-chloro-9-fluoro[1]benzothieno[3,2-d]-v-triazine
 4-chloro-7-methyl[1]benzothieno[3,2-d]-v-triazine
 9-bromo-4-chloro[1]benzothieno[3,2-d]v-triazine
 4,6-dichloro[1]benzothieno[3,2-d]-v-triazine
 4-chloro-7-nitro[1]benzothieno[3,2-d]-v-triazine
 4-chloro-9-methyl[1]benzothieno[3,2-d]-v-triazine
 4,8-dichloro[1]benzothieno[3,2-d]-v-triazine
 4-chloro-7-fluoro[1]benzothieno[3,2-d]-v-triazine
 4-ethoxy[1]benzothieno[3,2-d]-v-triazine
 4-ethylamino[1]benzothieno[3,2-d]-v-triazine
 4-diethylamino[1]benzothieno[3,2-d]-v-triazine The compounds of this invention are prepared by the simple but unexpected and novel process of this invention, which comprises diazotizing an appropriately phenyl-substituted 3-aminobenzo[b]thiophene-2-carbonitrile, the synthesis of which was taught by Beck et al. 1974, supra, with an alkali metal nitrite and hydrochloric acid at from about −10° C. to about 25° C. The product of the diazotization is the correspondingly phenyl-substituted 4-chloro[1]benzothieno[3,2-d]-v-triazine, from which other compounds, having the desired R substitutents, are readily prepared.

The process is preferably used for preparing compounds wherein $R^1$ represents hydrogen, chloro or nitro.

The expected product of the diazotization is merely the diazonium salt. According to the prior art, one would expect that such a salt could be reduced and cyclized to the 3-aminobenzothieno[3,2-c]pyrazole, or converted to the phenol or the chloride. Taylor & McKillop, The Chemistry of Cyclic Enaminonitriles and o-Aminonitriles 225–26 (Interscience 1970); Kwartler et al., *J. Am. Chem. Soc.* 65, 1804–06 (1943); Fieser & Fieser, Advanced Organic Chemistry 727–28 (Reinhold 1961). Unexpectedly, however, the benzothienotriazines are produced in good yield by the diazotization, without further steps.

Sodium nitrite is the preferred alkali metal nitrite, although potassium nitrite and lithium nitrite are also quite effective. As chemists will understand, other diazotization reagents, such as alkyl nitrites and the like, can likewise be used in particular circumstances.

The preferred temperature for the diazotization is from about −5° C. to about 5° C. Ice bath temperature is the most convenient and widely-used temperature for diazotizations, including the present process.

The reaction medium used in the diazotization must contain a substantial amount of concentrated hydrochloric acid, which serves both as a reactant and as a reaction solvent. It is possible to dilute the concentrated acid with water, up to about one-third of the amount of acid, without harming the yield of the diazotization.

Addition of a concentrated alkanoic acid to the reaction medium is a preferred technique. Propionic acid, butyric acid, and, preferably, glacial acetic acid, can be used. The role of an alkanoic acid is probably to homogenize the reaction mixture. Whatever the mechanism may be, addition of an amount of alkanoic acid up to the amount of concentrated hydrochloric acid is desirable.

Each molar unit of product produced by the diazotization consumes one molar unit each of the benzothiophene starting compound, the nitrite and the hydrochloric acid. Most economical operation of the process, of course, occurs when approximately equal molar quantities of the reactants are supplied. Some product will be produced so long as any quantities of the three reactants are present, however.

The process usually goes to completion in about one hour, or even less. In general, however, reaction times from about 15 minutes to about 3 hours can be used.

The reactions used to convert the 4-chloro compound prepared by the novel diazotization to the other 4-substituted compounds are common in organic chemistry. For example, methoxy and ethoxy-substituted compounds are prepared by displacing the chlorine atom with an alkali metal alkoxide. The various amine-substituted compounds are prepared by reaction with the appropriate amine in any convenient reaction solvent. The 4-unsubstituted compound is prepared by oxidation of the 4-hydrazino derivative with mercuric oxide in water.

All of the reactants are readily obtainable with the ordinary knowledge of organic chemists.

The following preparative examples are shown to assure that a chemist will have no difficulty in obtaining the present compounds, or in carrying out the process of this invention. The products of the following examples were identified by nuclear magnetic resonance analysis, elemental microanalysis, and, in some instances, by mass spectroscopy.

EXAMPLE 1

4-chloro[1]benzothieno[3,2-d]-v-triazine

A 4.4 g. portion of 3-aminobenzo[b]thiophene-2-carbonitrile was suspended in 60 ml. of concentrated hydrochloric acid. The mixture was cooled in an ice bath, and was then stirred vigorously while 2.1 g. of sodium nitrite in 20 ml. of water was added dropwise. After the addition was complete, the mixture was allowed to warm to room temperature over a 2-hour period, while stirring was continued. The mixture was then poured over ice, and the precipitated product was recovered by filtration. Recrystallization from dimethylformamide-water produced 4.2 g. of 4-chloro[1-]benzothieno[3,2-d]-v-triazine, m.p. 160°–162° C.

|   | Theoretical | Found |
|---|---|---|
| C | 48.77% | 48.35% |
| H | 1.82 | 1.96 |
| N | 18.96 | 19.08 |

EXAMPLE 2

4,9-dichloro[1]benzothieno[3,2-d]-v-triazine

Following the general scheme of Example 1, 8.8 g. of 3-amino-4-chlorobenzo[b]thiophene-2-carbonitrile was diazotized with 3.2 g. of sodium nitrite in 60 ml. of concentrated hydrochloric acid and 60 ml. of glacial acetic acid. The product was recrystallized from dimethylformamide to yield 8.2 g. of 4,9-dichloro[1]benzothieno[3,2-d]-v-triazine, m.p. 190°–192° C.

|   | Theoretical | Found |
|---|---|---|
| C | 42.21% | 42.41% |
| H | 1.18 | 0.98 |
| N | 16.41 | 16.62 |

EXAMPLE 3

4-chloro-9-nitro[1]benzothieno[3,2-d]-v-triazine

The process of Example 2 was followed in general, using 4.4 g. of 3-amino-4-nitrobenzo[b]thiophene-2-carbonitrile and 1.7 g. of sodium nitrite in 60 ml. of concentrated hydrochloric acid and 60 ml. of glacial acetic acid. The product was recrystallized from a dimethylformamide, and the yield was 4.0 g. of purified 4-chloro-9-nitro[1]benzothieno[3,2-d]-v-triazine, m.p. 171°–173° C.

|   | Theoretical | Found |
|---|---|---|
| C | 40.54% | 40.75% |
| H | 1.13 | 1.35 |
| N | 21.01 | 21.25 |

EXAMPLE 4

4-methoxy[1]benzothieno[3,2-d]-v-triazine

A 2.2 g. portion of the product of Example 1 was stirred at reflux temperature in 100 ml. of methanol with 0.7 g. of sodium methoxide for one hour. When the reaction mixture was cooled, the product, 1.9 g. of 4-methoxy[1]-benzothieno[3,2-d]-v-triazine, m.p. 165°–167° C., crystallized and needed no further purification.

|   | Theoretical | Found |
|---|---|---|
| C | 55.29% | 55.05% |
| H | 3.25 | 3.47 |
| N | 19.34 | 19.25 |

EXAMPLE 5

4-hydrazino[1]benzothieno[3,2-d]-v-triazine

A 2.5 g. portion of the product of Example 1 was refluxed with 10 ml. of hydrazine hydrate in 75 ml. of denatured ethanol for 2 hours. The solution was chilled at about 4° C. for 2 days, and was then filtered. The separated solids were recrystallized from dimethylformamide-water to produce 1.3 g. of 4-hydrazino[1]benzothieno[3,2-d]-v-triazine, m.p. 194°–196° C.

|   | Theoretical | Found |
|---|---|---|
| C | 49.76% | 49.99% |
| H | 3.25 | 3.27 |
| N | 32.24 | 32.43 |

EXAMPLE 6

4-dimethylamino[1]benzothieno[3,2-d]-v-triazine

Dimethylamine gas was bubbled into a solution of 2.0 g. of the product of Example 1 in 50 ml. of dimethylformamide at about 100° C. for about 1½ hours. The solution was cooled to room temperature, and then was chilled at about 4° C. for 3 hours. The product which crystallized from the solution was collected and identified as 1.3 g. of 4-dimethylamino[1]benzothieno[3,2-d]-v-triazine, m.p. 207°–209° C.

|   | Theoretical | Found |
|---|---|---|
| C | 57.37% | 57.43% |
| H | 4.38 | 4.61 |
| N | 24.33 | 24.27 |

EXAMPLE 7

[1]benzothieno[3,2-d]-v-triazine

A 2.1 g. portion of the 4-hydrazino product of Example 5 was suspended in 130 ml. of water containing 5.4 g. of mercuric oxide and the mixture was stirred at reflux temperature for 4 hours. The mixture was then cooled and filtered, and the solids were triturated with hot ethyl acetate. After filtration, the filtrate was evaporated under vacuum. The residue was redissolved in ethyl acetate-hexane and was chromatographed over a silica gel column with 1:1 ethyl acetate-hexane as the eluant. The second product off the column was the desired product, which was recrystallized from denatured ethanol-water. The yield was 1.0 g. of [1]benzothieno[3,2-d]-v-triazine, m.p. 190°–191° C.

|   | Theoretical | Found |
|---|---|---|
| C | 57.74% | 57.82% |
| H | 2.67 | 2.81 |
| N | 22.44 | 22.41 |

EXAMPLE 8

4-methylamino[1]benzothieno[3,2-d]-v-triazine

Methylamine gas was bubbled through a refluxing solution of 4.4 g. of the product of Example 1 in 100 ml. of denatured ethanol for 1 hour. The solution was then allowed to cool to room temperature and stand overnight. The product crystallized spontaneously, and was recovered by filtration and recrystallized from ethanol-water to produce 3.0 g. of 4-methylamino[1-]benzothieno[3,2-d]-v-triazine, m.p. 231°–232° C.

|   | Theoretical | Found |
|---|---|---|
| C | 55.54% | 55.81% |
| H | 3.73 | 4.02 |
| N | 25.91 | 25.93 |

The compounds of this invention have valuable activity in the control of a variety of microscopic organisms, including bacteria, fungi, viruses and algae. For example, the compounds have been found to be effective inhibitors of the replication of algae such as chlorella, scenedesmus and anacystis.

Further, the compounds have controlled such typical protozoa as *Ochromonas malhamensis*, *Trichomonas vaginalis*, *Euglena gracilis*, and *Tetrahymena pyriformis*. Such harmful viruses are controlled as echo 10, Maryland B, vaccinia, Semliki forest, Ann Arbor influenza, herpes, polio III, and rhinovirus.

Further, the compounds control such phytopathogenic fungi as *Erysiphe polygoni*, *Colletotrichum langenarium*, *Plasmopara viticola* and *Cercospera beticola*, and such additional harmful pathogens as *Staphylococcus aureus*, *Erwinia amylovora*, *Candida tropicalis*, *Tricophyton metagrophytes*, *Aspergillus flavus* and *Ceratocystis ulmi*.

Thus, the compounds may be used for the sterilization and cleansing of surfaces and areas such as hospital environments, kitchen environments and houshold walls and floors by combining one or more of the compounds with soaps, detergents and cleansing agents and using the products in the conventional manner for the cleansing, sanitation and sterilization of such surfaces and areas. Further, the compounds may be used for the protection of plants from the attacks of phytopathogens by application of the compounds to the foliage of the plants to be treated, and for the inhibition of algae in water reservoirs and circulating systems.

I claim:
1. A compound of the formula

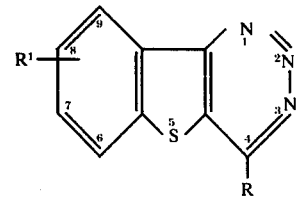

wherein R represents
hydrogen,
chloro,
methoxy,
ethoxy,
amino,
hydrazino,
methylamino,
ethylamino,
dimethylamino or
diethylamino;
$R^1$ represents
hydrogen,
chloro,
fluoro,
bromo,
methyl or nitro;

provided that R¹ represents hydrogen when R represents a group other than chloro.

2. The compound of claim 1 which is 4-chloro-[1]benzothieno[3,2-d]-v-triazine.

3. The compound of claim 1 which is 4-methoxy[1-]benzothieno[3,2-d]-v-triazine.

4. The compound of claim 1 which is 4-methylamino[1]benzothieno[3,2-d]-v-triazine.

5. The compound of claim 1 which is 4-dimethylamino[1]benzothieno[3,2-d]-v-triazine.

6. The compound of claim 1 which is [1]benzothieno[3,2-d]-v-triazine.

7. A process for the synthesis of a compound of claim 1 wherein R represents chloro which comprises contacting a compound of the formula

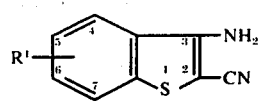

with an alkali metal nitrite and hydrochloric acid at a temperature from about −10° C. to about 25° C.

8. The process of claim 7 in which the temperature is from about −5° C. to about 5° C.

9. The process of claim 7 in which glacial acetic acid is present.

10. The process of claim 8 in which glacial acetic acid is present.

11. The process of claim 7 in which the alkali metal nitrite is sodium nitrite.

12. The process of claim 11 in which R¹ represents hydrogen.

13. The process of claim 11 in which R¹ represents chloro.

14. The process of claim 11 in which R¹ represents nitro.

* * * * *